(12) United States Patent
Bazinet et al.

(10) Patent No.: US 7,510,736 B2
(45) Date of Patent: Mar. 31, 2009

(54) METHOD FOR SELECTIVELY AND SEQUENTIALLY EXTRACTING CATECHINS FROM GREEN TEA LEAF

(75) Inventors: Laurent Bazinet, L'Ancienne-Lorette (CA); David Labbé, Sainte-Famille (CA); Angelo Tremblay, Charlesbourg (CA)

(73) Assignee: Université Laval, Québec (CA)

( * ) Notice: Subject to any disclaimer, the term of this patent is extended or adjusted under 35 U.S.C. 154(b) by 887 days.

(21) Appl. No.: 10/772,307

(22) Filed: Feb. 6, 2004

(65) Prior Publication Data
US 2005/0176939 A1 Aug. 11, 2005

(51) Int. Cl.
*A23F 3/00* (2006.01)
(52) U.S. Cl. .................. 426/435; 426/597; 426/590; 426/431
(58) Field of Classification Search ............. 426/597, 426/590, 431, 435
See application file for complete search history.

(56) References Cited

U.S. PATENT DOCUMENTS

| | | | | |
|---|---|---|---|---|
| 3,451,823 | A * | 6/1969 | Mishkin et al. | 426/312 |
| 4,613,672 | A * | 9/1986 | Hara | 549/399 |
| 4,680,193 | A | 7/1987 | Lunder et al. | |
| 5,198,259 | A * | 3/1993 | Hoogstad | 426/435 |
| 5,683,736 | A * | 11/1997 | Lunder | 426/597 |
| 6,120,825 | A * | 9/2000 | Cirigliano et al. | 426/435 |
| 6,210,679 | B1 * | 4/2001 | Bailey et al. | 424/729 |
| 2004/0265404 | A1 * | 12/2004 | Baraldi | 424/774 |

FOREIGN PATENT DOCUMENTS

| | | | |
|---|---|---|---|
| CN | 98104564.2 | | 9/1999 |
| CN | 99104206.9 | | 1/2000 |
| CN | 01106878.7 | | 9/2002 |
| CN | 02139219.6 | | 6/2003 |
| JP | 4-164030 | * | 6/1992 |
| JP | 7-70105 | * | 3/1995 |
| JP | 2003-219799 | | 8/2003 |

OTHER PUBLICATIONS

Worth et al. Analysis of catechins and caffeine in tea extracts by micellar electrokinetic chromatography. Electrophoresis. 2000. vol. 21. pp. 3634-3638.*
Chen et al. Preparation of flavanol-rich green tea extract by precipitation iwth ALCL3. Journal of the Science of Food and Agriculture. 2001. vol. 81. pp. 1034-1038.*
Copeland E.L. et al., 1998, Food Chemistry, 61: 81-87.
Du Q.-Z. et al., 1998, J. Liq. Chrom. & Rel. Technol., 21: 203-208.
Labbé et al., "Effect of brewing temperature and duration on green tea catechin solubilization: Basis for production of EGC and EGCG-enriched fractions", Separation and Purification Technology 49 (2006) 1-9. Available online at www.directscience.com.
Bazinet et al., "Production of green tea EGC- and EGCG-enriched fractions by a two-step extraction procedure", Separation and Purification Technology 56 (2007) 53-56. Available online at www.directscience.com.
Kilmartin et al., "Characterisation of polyphenols in green, oolong, and black teas, and in coffee, using cyclic voltammetry", Food Chemistry 82 (2003) 501-512. Available online at www.directscience.com.

* cited by examiner

*Primary Examiner*—Anthony Weier
(74) *Attorney, Agent, or Firm*—Ogilvy Renault, LLP

(57) ABSTRACT

The present invention provides a method for specifically and sequentially purifying catechins from a plant product. More particularly, the present invention provides a method for purifying EGC and EGCG from green tea leaves by sequential brewing at different brewing temperature and for specific infusion times.

9 Claims, 8 Drawing Sheets

METHOD FOR SELECTIVELY AND SEQUENTIALLY EXTRACTING CATECHINS FROM GREEN TEA LEAF

BACKGROUND OF THE INVENTION (a) Field of the Invention

The present invention relates to a method for selectively and sequentially extracting catechins from a plant product, and more particularly from green tea leaves.

(b) Description of Prior Art

Tea is the second most consumed beverage around the world, after water, for its attractive aroma and flavor, as well as for its health-related benefits. The health-related benefits attributed to tea are antioxidant properties, stimulation of detoxification (phase II) enzyme activity, inhibition of transcription factor activation, inhibition of cell-signaling pathways, induction of apoptosis, cell cycle regulation, inhibition of cell invasion and angiogenesis, and interference with receptor binding.

For many years, numerous works were carried out to characterize the composition of tea infusions responsible for those health-related benefits. A typical green tea infusion, i.e. 1 gram of tea leaves in 100 mL of water for a three (3) minutes brew, comprises approximately 250 mg of solids, wherein approximately 30% are catechins, while a black tea infusion catchechin content is approximately 9%.

Catechins are colourless, water-soluble compounds which impart bitterness and astringency to tea infusion. These molecules belong to flavonoids, which are plant secondary metabolites distributed in the plant kingdom. Flavonoids can be subdivided into six classes: flavones, flavanones, isoflavones, flavonols, flavanols and anthocyanins based on the structure and conformation of the heterocyclic oxygen ring (C ring) of the basic molecule. Tea catechins are primarily flavanols and more principally epicatechin (EC), epigallocatechin (EGC), epicatechin gallate (ECG), and epigallocatechin gallate (EGCG). EGCG is regarded as the most important of the tea catechins because of its high content in tea and the fact that its activity is mirrored by green tea extracts.

Methods for producing tea extracts with high EGCG ratios have been reported in the prior art (Copland et al., 1998. Food Chem. 61:81-87). Du et al. (Du et al., 1997. res. Develop. Basic Agric. and High Technol., 1:40-47; Du et al., 1998. J. Liq. Chromatog. & Related Technol., 21:203-208) reported the use of high-speed counter-current chromatography (HSCCC) as fractionation tool for both crude extracts and semi-purified fractions as well as for the production of purified catechin from crude green tea extracts.

Patent application CN 141426, Applicant HUBEI Provincial Institute of Chemistry, reports a process for preparing tea polyphenol with high catechin content and low caffeine content that comprises an alcohol precipitation step and an alcohol co-precipitation step.

Patent application CN 1370766, Applicant Zhongnan University, reports a pollution-free polyphenol extraction process from tea that comprises salting out a tea infusion using a polyamide as adsorbent and separating polyphenols from caffeine and pigment using an acid aqueous solution of citric acid as washing agent.

Methods for the extraction of flavonoids or catechins from sources other than tea leaves are also known in the art. For example, patent application CN 1241447, Applicant Zhejiang University, reports a flavonoid extraction process from scutellaria root. This process comprises leaching out flavonoids from scutellaria roots with a water solution containing an ethylene oxide-propane oxide random copolymer (EOPO) and ethanol. This step is followed by subsequent concentration and purification steps, including a temperature changing counter-extraction process.

Patent application CN 1228968 reports a method for extracting flavonoid compounds from bamboo leaves that comprises a thermal reflux extraction of bamboo leaves with low-concentration low-grade alcohol. This step is completed by a concentration step, a separation and refining step by liquid-liquid extraction using middle-grade alcohol and finally, drying.

Although the above-mentioned methods may lead to the obtention of high yield catechins and other flavonoids from plant extracts, they required the use of organic solvent or adsorbent or are restricted to the purification of limited quantities of catechins, especially when a liquid chromatography (HSCCC) is required. Therefore, these methods are not easily transposable to the industrial scale since they are not environmentally nor economically advantageous. Moreover, in an industrial context of producing a catechin extract or an EGCG-enriched fraction, an important step is the solubilization of catechins from tea leaves.

Kinetics and equilibria of black tea infusion have been widely studied by Spiro et al. until recently. However, it is widely established in the prior art that the polypheriol content of black tea significantly differs from that of green tea. Fresh tea leaves are rich in catechins. Tea leaves also contain polyphenol oxidase enzymes in separate compartments from catechins. When tea leaves are rolled or broken up during industrial manufacture, catechins contact polyphenol oxidase, joining them to one another and forming theaflavins and thearubigins. These oxidized tea polyphenols give oolong and black tea their distinct flavors and colors. Steaming or pan firing inactivates the polyphenol oxidase enzyme. During its manufacture, white and green tea is steamed to inactivate polyphenol oxidase and is then dried. Thus, white and green tea contains higher concentrations of catechins. In contrast, black tea is highly oxidized, resulting in increased concentrations of theaflavins and thearubigins and relatively low catechin concentrations, while oolong tea is only partially oxidized. The flavonol content is less affected by processing, and flavonols are present in comparable quantities in white, green, oolong, and black teas. On the aspect of solubilization kintetics and equilibra of catechin, very little basic scientific data are available on the technology of brewing of green tea, which may significantly differ from black tea.

Since green tea represent a much proper raw material for obtaining large amounts of catechins, it would be highly desirable to be provided with a environmentally-friendly and economical method, that is transposable to an industrial scale for producing catechin enriched fractions from green tea leaves.

SUMMARY OF THE INVENTION

One aim of the present invention is to provide a method for selectively and sequentially extracting at least two catechins from a plant product. This method comprises submitting the plant product to a first brew at a first brewing temperature and for a sufficient period of time to allow the extraction of most of at least one first catechin. The treated plant product is collected and further submitted to a second brew at a second brewing temperature and for a sufficient period of time to allow the extraction of at least one second catechin.

DESCRIPTION OF PREFERRED EMBODIMENTS

Figure 1:
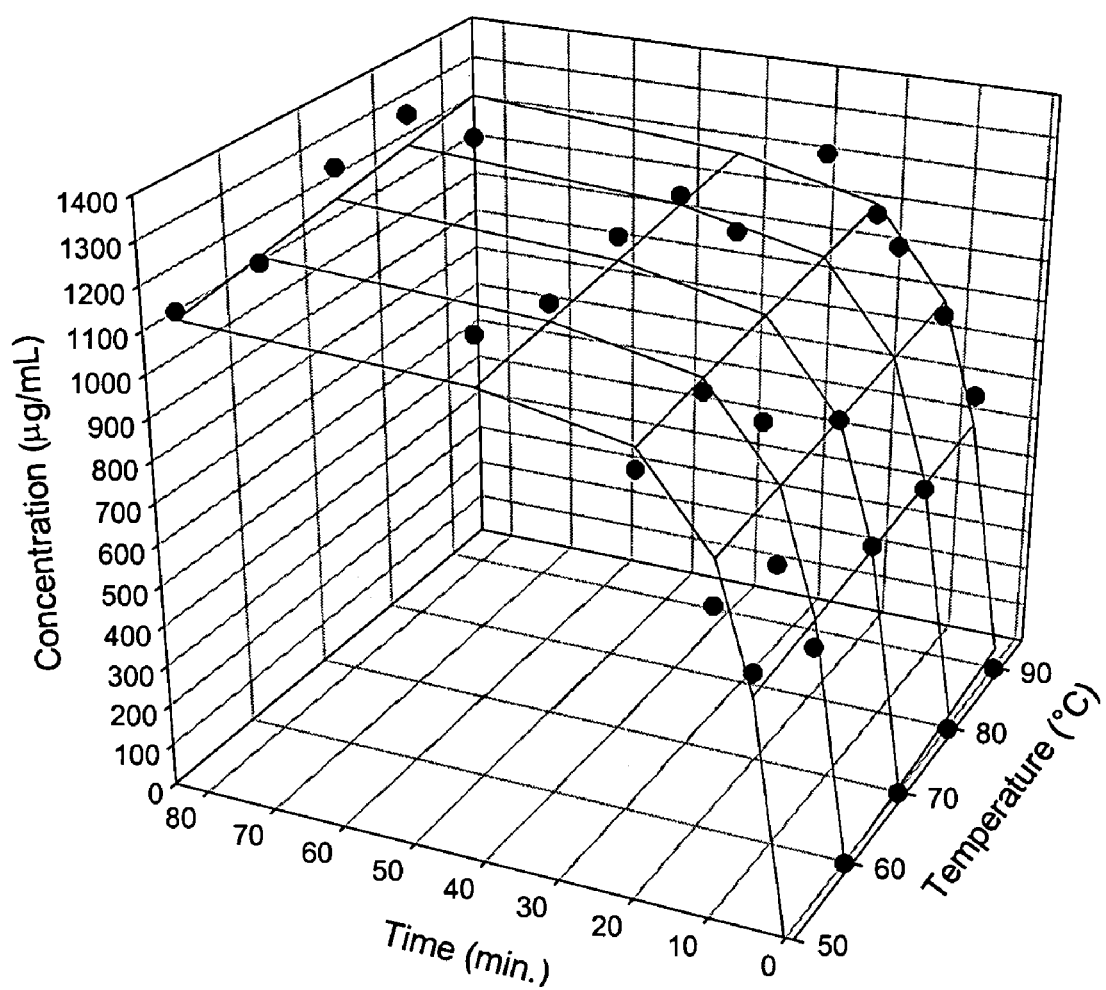
FIG. 1 shows the variation of epigallocatechin (EGC) concentration of a green tea infusion as a function of brewing time and brewing temperature.

According to the present invention, there is provided a method for selectively and sequentially extracting EGC and EGCG from green tea leaves. The method of the present invention relies on the differential temperature and time of infusion of catechins in water to separately extract EGC and EGCG. A person skilled in the art will know that other catechins may be extracted based on their solubility. For example, EC, GCG, ECG and C may be extracted concomitantly with EGC or EGCG.

EGC is highly soluble from 50 to 90° C., where two-thirds of the total amount of EGC of green tea leaves is found in solution after a 10 minutes brew. Therefore, the extraction of EGC from green tea leaves can be performed at brewing temperatures that range from 50 to 90° C. At the opposite, EGCG is less soluble at 50° C. and therefore, needs more time to be significantly found in solution. After a 10 minutes brew, only 10 percent of the total EGCG is found in solution, in comparison with 100% after a forty minutes brew, while two-thirds of EGCG is found after a 10 minutes brew at 90° C. Based on that premise, EGC and EGCG can be selectively and sequentially extracted. In a preferred embodiment, green tea leafs are submitted to a first brew at 50° C., for a ten minutes period. This first brew allows the solubilisation of most of EGC into water, with solubilisation of a minimal amount of EGCG. The green tea leaves are then removed from the first infusion and submitted to a second brew, at 90° C. for ten minutes. Since the most of the EGC has been removed from the green tea leaves during the first brew, the remaining EGCG is solubilized without significant quantities of EGC during the second brew. A skilled artisan will understand that sequential brewing temperatures and times may vary and that they are not restricted to the above-mentioned conditions. For example, a skilled artisan could perform the first infusion at 40° C. for 15 minutes, followed by a second infusion at 80° C. for 25 minutes. It is therefore an embodiment of the present invention to provide a method in which the first brew temperature is below 65° C., and more preferentially between 20° C. and 60° C., while the second brew temperature is above 65° C., and more preferentially between 70° C. and 90° C.

The plant product used for the purpose of the present invention is preferably tea leaf. More particularly white tea leaves or green tea leaves are preferred since their EGCG content is the most interesting among plant products. The present invention is however not restricted to tea products. For example, fruits such as grape, apple, apricot, blackberry, or cherry or products from scutellaria and bamboo, could be used as raw materials to obtain EGCG.

In a preferred embodiment of the present invention an aqueous solution is used for the brewing operations, and more preferably water. Salts or other material that favors solubilization of catechins may be added to the aqueous solution.

The present invention will be more readily understood by referring to the following examples which are given to illustrate the invention rather than to limit its scope.

EXAMPLES

Example 1

Determination of Catechin Solubilisation as a Function of the Brewing Temperature and Time Material Green Tea The green tea was a non-biological Japanese green tea (lot 12423TKA) obtained from local retailer (La Giroflée, Quebec City, QC, Canada). The green tea was stored at room temperature in a dark and dry space.

Catechin and Caffein Standards (+)-catechin HPLC grade standard was obtained from Indofine (Hillsborough, N.J., U.S.A.) while (−)-epicatechin, (−)-epigallocatechin, (−)-epicatechin gallate, (−)-epigallocatechin gallate, (−)-gallocatechin gallate and caffein standards were from Sigma Company (Saint-Louis, Mo., U.S.A.).

Method

Protocol 20 g of green tea were brewed in 1000 mL of double-distilled water to performe catechin solubilization, in accordance with the standards known in the art of 1 g of tea per 50 mL of water. Brews were performed in a water bath at five (5) different temperatures, namely 50, 60, 70, 80 and 90° C. Ten (10) mL samples were taken from each brews after 0, 5, 10, 20, 40 and 80 minutes of brewing, they were then rapidly cooled down and stored at 4° C. until analyses. Conductivity, pH and caffeine and catechin concentrations were determined for each sample.

Determination of Catechin and Caffeine Concentration

Each sample of green tea collected during brewing were filtered through a 0.20 μm filter (Aerodisc LC13 PVDF, Gelman Laboratory, Ann Arbor, Mich., U.S.A.) and diluted with HPLC grade water to be analyzed. Standard curves were calculated from a mixture of flavanols and caffeine compounds at different concentrations. Correlations obtained ranged from 0.99808 to 0.99954. The RP-HPLC method was based on the National Institute of Standards and Technology method. The RP-HPIC system used for the purpose of the present invention is described as follow:

Column: YMC-Pack ODS-AM, S-5 μm, 12 nm, 250×4.6 mm I.D.
Guard-column: YMC ODS-AM S-5 120 Å 4.0×20 mm DC Guard Cartridge
Pump: Beckman, System Gold programmable solvent module 126
Detector: Beckman, System Gold programmable detector module 116
Auto-injector: LKB Bromma 2157 autosampler
Software: Gold v8.10
Phase A: Water+0.05% TFA
Phase B: Acetonitrile+0.05% TFA Detection of the analytes was carried out with UV detection system, at 210 nm. The column temperature was maintained at 40° C. throughout analyses. The mobile phases were filtered through a 0.2 μm nylon filter (Mendel Scientific Compagnie, Guelph, Canada). Details on gradient used are shown in Table 1.

TABLE 1

Gradient used for HPLC

| Time (min) | % B |
|---|---|
| 0 | 12.0 |
| 22 | 19.9 |
| 32 | 100.0 |
| 42 | 12.0 |

Statistical Analysis

Data on catechins and caffein were subject to an analysis of variance using Sigma Stat software (version 2.0 pour Windows, SPSS inc., Chicago, Ill.).

Results (−)-Epigallocatechin (EGC) Concentration

Solubilisation of EGC is significantly increased between 0 and 20 min, after which it becomes stable, notwithstanding the infusion temperature (FIG. 1 and Table 2). Concentrations at 70° C. of 0 μg/mL at time 0 min, 602.2 μg/mL after 5 min and 849.5 μg/mL after 20 min were observed.

TABLE 2

Catechins and caffein concentration (μg/mL) in a green tea brewing as a function of time and temperature.

| Temperature (° C.) | Time (min) | EGC Mean | ±SD | C Mean | ±SD | Caff Mean | ±SD | EC Mean | ±SD | EGCG Mean | ±SD | GCG Mean | ±SD | ECG Mean | ±SD |
|---|---|---|---|---|---|---|---|---|---|---|---|---|---|---|---|
| 50 | 0 | 0.0 | 0.0 | 0.0 | 0.0 | 0.0 | 0.0 | 0.0 | 0.0 | 0.0 | 0.0 | 0.0 | 0.0 | 0.0 | 0.0 |
|  | 5 | 608.3 | 75.9 | 4.6 | 1.0 | 147.8 | 17.8 | 75.6 | 12.3 | 15.5 | 26.9 | 0.0 | 0.0 | 0.0 | 0.0 |
|  | 10 | 739.7 | 131.3 | 5.9 | 0.8 | 170.8 | 30.3 | 88.7 | 15.6 | 77.2 | 30.9 | 0.0 | 0.0 | 0.0 | 0.0 |
|  | 20 | 1004.3 | 333.6 | 6.3 | 1.4 | 241.9 | 65.6 | 120.6 | 35.3 | 245.3 | 46.4 | 0.0 | 0.0 | 7.6 | 8.9 |
|  | 40 | 1229.6 | 325.0 | 10.5 | 3.4 | 331.7 | 79.2 | 154.7 | 40.2 | 489.3 | 95.7 | 6.7 | 11.5 | 27.0 | 14.9 |
|  | 80 | 1160.6 | 52.4 | 10.0 | 0.4 | 337.8 | 26.4 | 147.8 | 11.4 | 542.6 | 41.7 | 6.6 | 11.4 | 33.9 | 25.5 |
| 60 | 0 | 0.0 | 0.0 | 0.0 | 0.0 | 0.0 | 0.0 | 0.0 | 0.0 | 0.0 | 0.0 | 0.0 | 0.0 | 0.0 | 0.0 |
|  | 5 | 508.3 | 92.0 | 4.2 | 0.0 | 128.1 | 35.3 | 63.9 | 16.2 | 104.6 | 53.1 | 0.0 | 0.0 | 0.0 | 0.0 |
|  | 10 | 684.8 | 103.3 | 5.5 | 0.7 | 183.7 | 32.3 | 82.7 | 12.3 | 177.1 | 63.9 | 0.0 | 0.0 | 10.8 | 7.9 |
|  | 20 | 1045.4 | 92.0 | 9.5 | 0.7 | 313.2 | 39.8 | 123.5 | 12.5 | 557.2 | 116.6 | 6.5 | 11.3 | 48.8 | 15.6 |
|  | 40 | 1181.5 | 144.6 | 11.5 | 2.5 | 380.9 | 65.8 | 137.7 | 18.8 | 858.7 | 240.0 | 0.0 | 0.0 | 79.4 | 26.8 |
|  | 80 | 1157.6 | 128.5 | 11.0 | 1.9 | 369.9 | 47.5 | 136.8 | 19.7 | 634.6 | 337.8 | 0.0 | 0.0 | 34.0 | 44.4 |
| 70 | 0 | 0.0 | 0.0 | 0.0 | 0.0 | 0.0 | 0.0 | 0.0 | 0.0 | 0.0 | 0.0 | 0.0 | 0.0 | 0.0 | 0.0 |
|  | 5 | 602.2 | 115.2 | 5.8 | 1.4 | 232.7 | 35.0 | 72.8 | 10.2 | 347.8 | 80.1 | 0.0 | 0.0 | 30.9 | 7.5 |
|  | 10 | 886.0 | 21.7 | 8.7 | 0.9 | 327.1 | 10.2 | 101.5 | 4.2 | 613.3 | 66.6 | 0.0 | 0.0 | 56.0 | 9.5 |
|  | 20 | 849.5 | 136.3 | 8.9 | 2.4 | 296.0 | 53.3 | 96.1 | 16.7 | 702.0 | 181.2 | 11.2 | 19.3 | 69.4 | 21.6 |
|  | 40 | 1220.5 | 78.3 | 13.6 | 1.8 | 414.6 | 31.9 | 137.9 | 10.2 | 999.0 | 156.8 | 40.6 | 4.8 | 88.1 | 23.5 |
|  | 80 | 1276.5 | 131.2 | 15.1 | 2.2 | 443.3 | 54.1 | 149.8 | 18.1 | 1208.3 | 150.1 | 57.2 | 5.1 | 125.7 | 15.1 |
| 80 | 0 | 0.0 | 0.0 | 0.0 | 0.0 | 0.0 | 0.0 | 0.0 | 0.0 | 0.0 | 0.0 | 0.0 | 0.0 | 0.0 | 0.0 |
|  | 5 | 603.4 | 178.9 | 6.8 | 2.7 | 305.4 | 108.4 | 85.2 | 30.9 | 342.9 | 201.1 | 0.0 | 0.0 | 29.6 | 29.1 |
|  | 10 | 1172.0 | 243.0 | 10.6 | 0.4 | 408.3 | 28.6 | 148.1 | 20.7 | 483.4 | 327.6 | 19.0 | 17.8 | 32.7 | 37.1 |
|  | 20 | 1359.6 | 185.7 | 13.9 | 1.1 | 461.5 | 39.9 | 164.9 | 33.7 | 930.0 | 266.2 | 40.2 | 17.6 | 45.7 | 59.8 |
|  | 40 | 1212.2 | 340.3 | 14.6 | 4.8 | 408.5 | 112.5 | 145.0 | 45.2 | 1024.0 | 287.7 | 61.1 | 22.5 | 97.5 | 27.2 |
|  | 80 | 1307.4 | 255.6 | 20.4 | 3.8 | 457.4 | 72.9 | 161.9 | 40.1 | 1137.2 | 96.9 | 87.5 | 11.8 | 103.8 | 5.5 |
| 90 | 0 | 0.0 | 0.0 | 0.0 | 0.0 | 0.0 | 0.0 | 0.0 | 0.0 | 0.0 | 0.0 | 0.0 | 0.0 | 0.0 | 0.0 |
|  | 5 | 705.9 | 61.0 | 7.8 | 1.0 | 328.2 | 40.3 | 84.9 | 9.5 | 489.6 | 71.6 | 9.6 | 16.7 | 48.1 | 3.0 |
|  | 10 | 893.9 | 119.8 | 10.1 | 1.5 | 348.6 | 46.9 | 104.5 | 13.2 | 763.8 | 184.8 | 42.5 | 7.8 | 62.9 | 8.5 |
|  | 20 | 1116.5 | 82.5 | 15.1 | 1.0 | 391.8 | 32.6 | 129.2 | 10.6 | 1039.9 | 53.9 | 63.5 | 1.4 | 97.9 | 24.0 |
|  | 40 | 1019.6 | 227.9 | 17.1 | 4.6 | 359.3 | 90.8 | 119.1 | 27.2 | 1071.4 | 331.9 | 99.7 | 23.7 | 98.3 | 44.4 |
|  | 80 | 1153.5 | 101.5 | 28.1 | 3.0 | 433.0 | 50.7 | 140.5 | 14.7 | 1282.7 | 180.3 | 186.0 | 18.1 | 133.9 | 36.5 |

(+)-Catechin (C) Concentration

Figure 2:
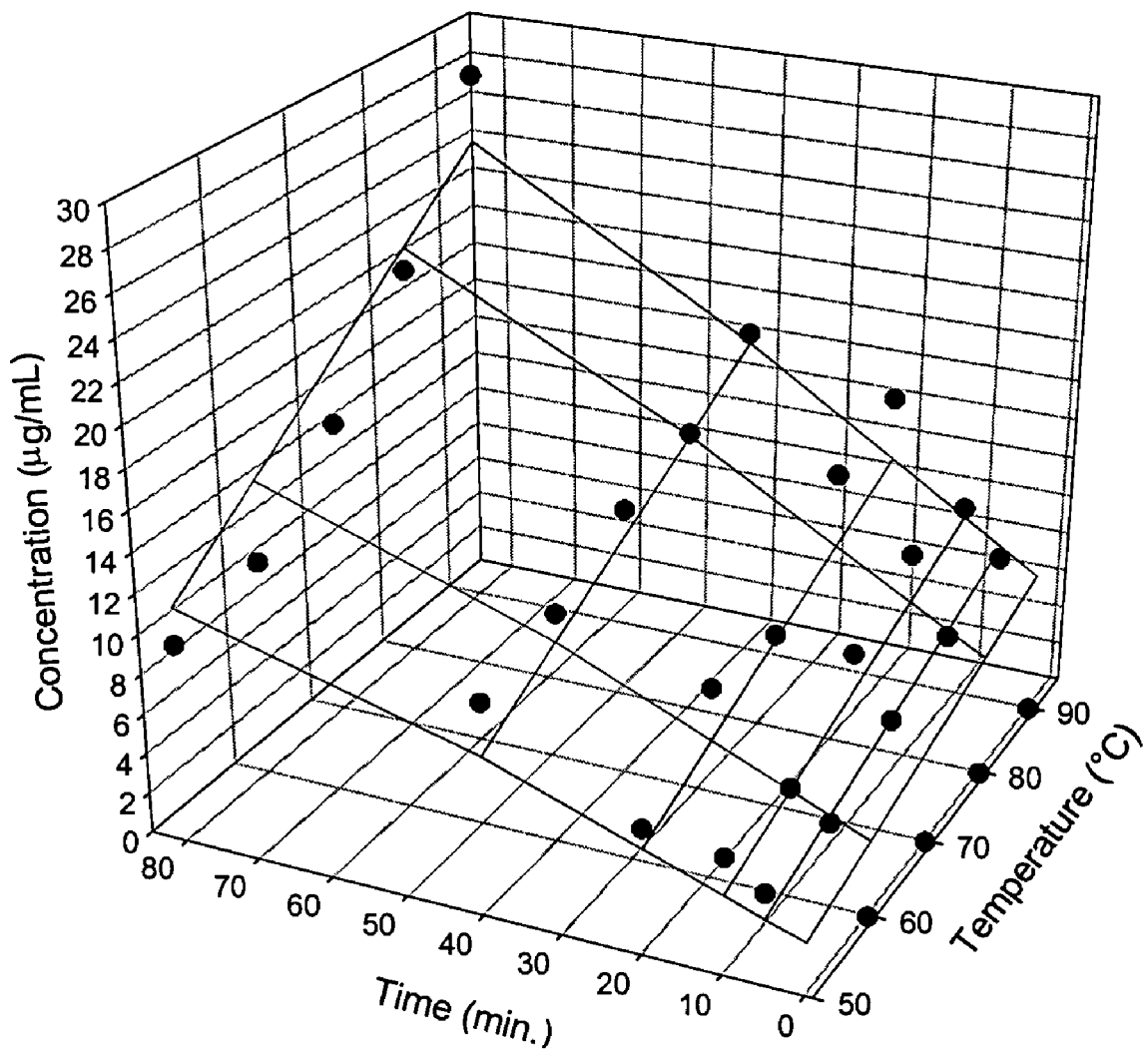
FIG. 2 shows the variation of catechin (C) concentration of a green tea infusion as a function of brewing time and brewing temperature.

Solubilisation of catechin is significantly increased with higher brewing temperatures (P<0.001) while being slightly affected by brewing time (FIG. 2 and Table 2). It is important to note that catechin is a relatively low abundant polyphenol within green tea infusion and that its concentration stays between 0 µg/mL and 28.1 µg/mL. Temperature and brewing time have a synergistic effect on catechin concentration since concentration increased linearly from 50° C. to 80° C., while increasing significantly at 90° C. (FIG. 2 and Table 2).

Caffeine Concentration

Figure 3:
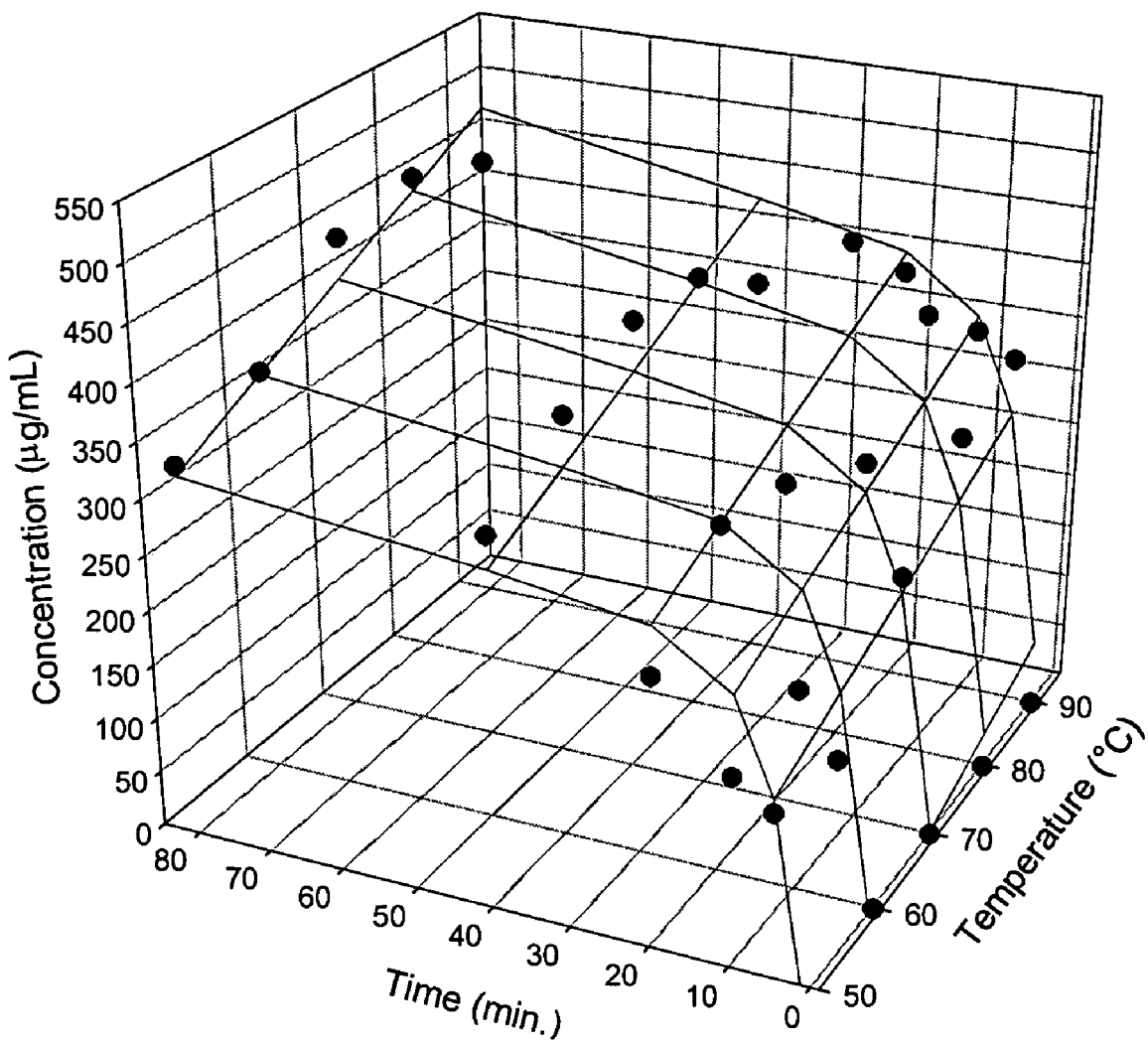
FIG. 3 shows the variation of caffeine (Caf) concentration of a green tea infusion au a function of brewing time and brewing temperature.

Caffeine solubilisation is slightly increased with brewing temperature and infusion time (FIG. 3 and Table 2). At 50° C., caffeine concentration ranges from 0 µg/mL at time 0 min to 331.7 µg/mL after 40 min. At 90° C., caffeine concentration ranges from 0 µg/mL. at time 0 min to reach 348.6 µg/mL after 10 min and slightly increases to 359.3 µg/mL after 40 min ($R2=0.970$).

(−)-Epicatechin (EC) Concentration

Figure 4:
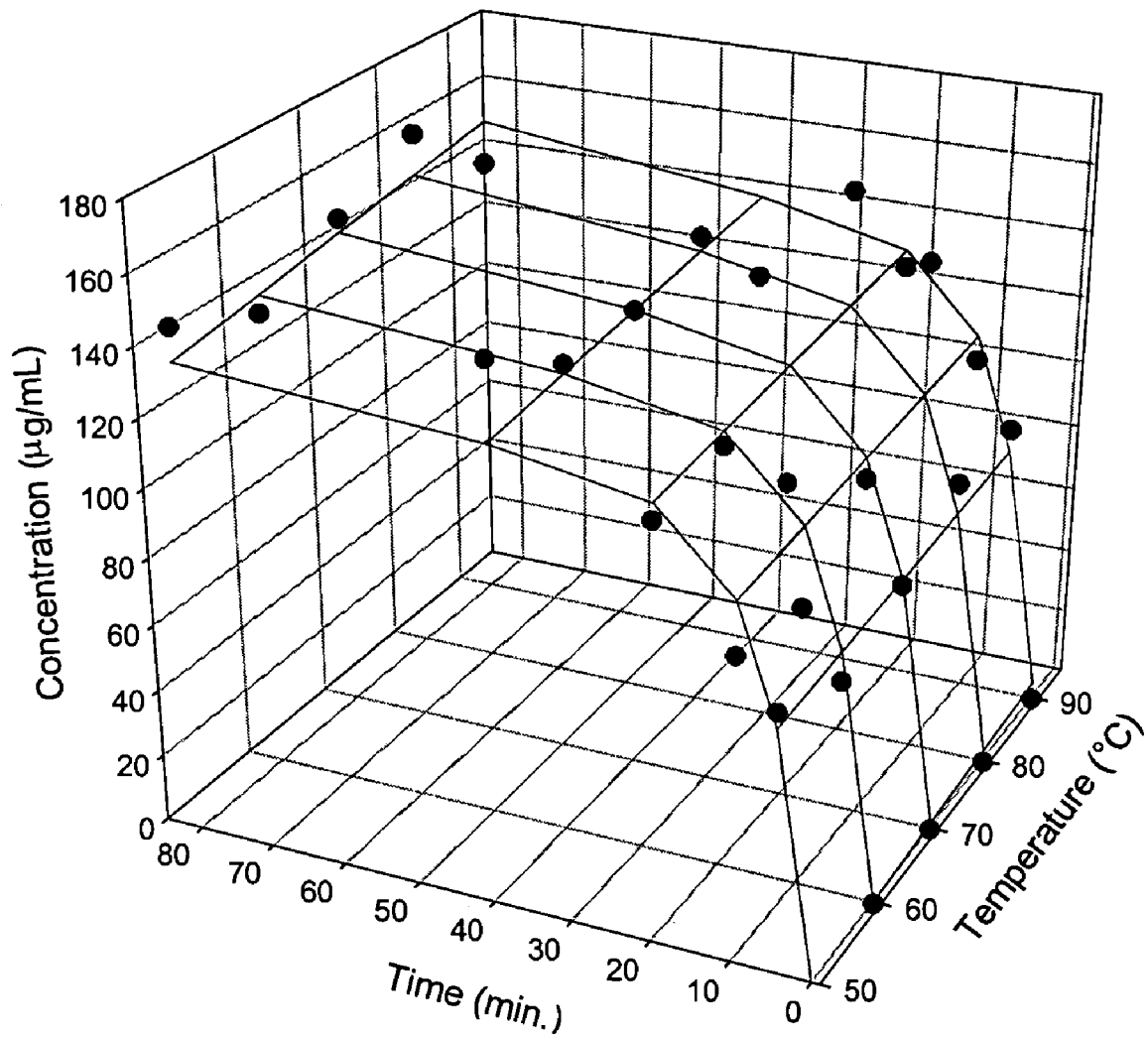
FIG. 4 shows the variation of epicatechin (EC) concentration of a green tea infusion as a function of brewing time and brewing temperature.

Solubilisation of EC increases substantially between 0 and 20 min, after which it becomes stable (FIG. 4 and Table 2). The brewing temperature does not affect significantly the solubilisation of EC. Concentrations were 0 µg/mL at 0 min, 85.2 µg/mL at 5 min and 164.9 µg/mL at 20 min, at a brewing temperature of 80° C.

(−)-Epigallocatechin Gallate (EGCG) Concentration

Figure 5:
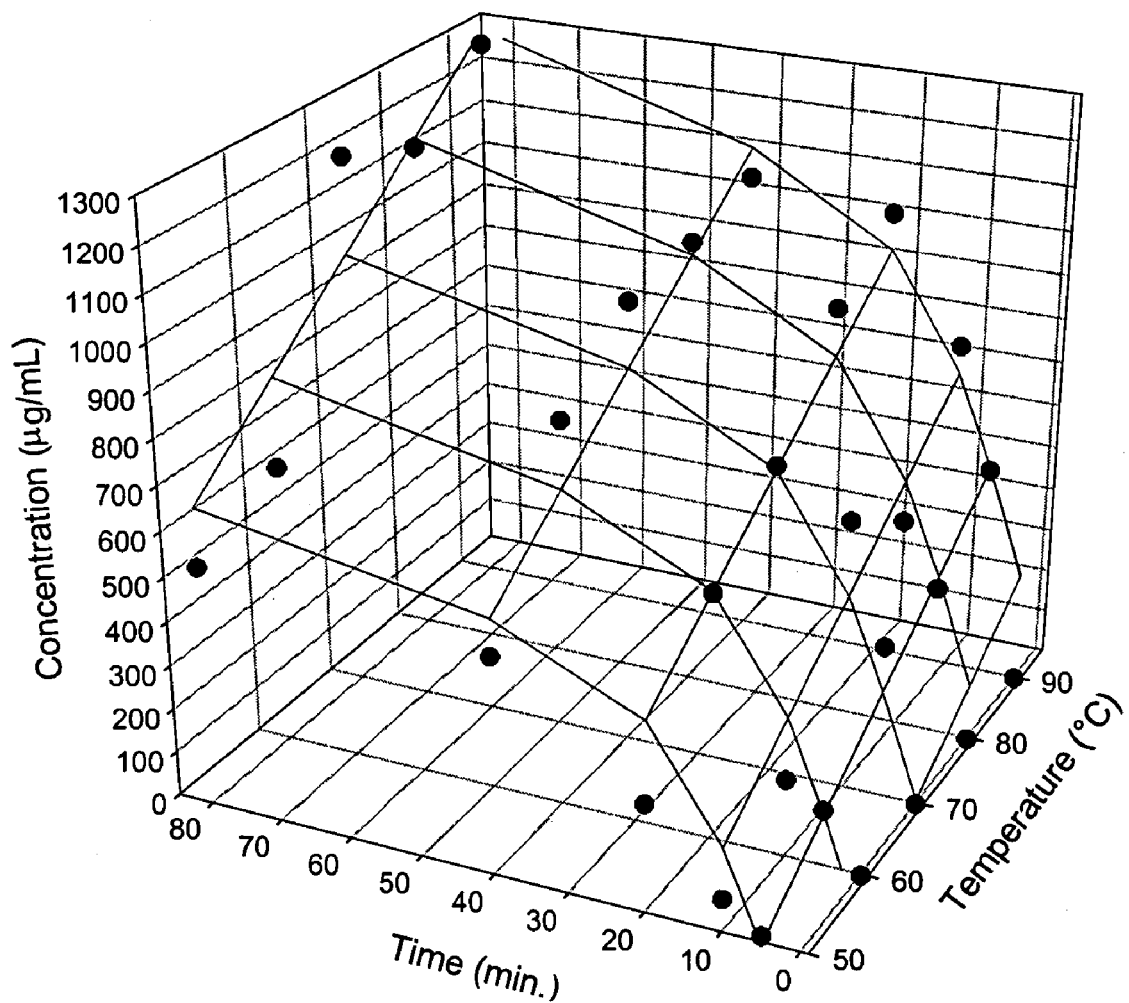
FIG. 5 shows the variation of epigallocatechin gallate (EGCG) concentration of a green tea infusion as a function of brewing time and brewing temperature.

Solubilisation of EGCG is intimately bound to temperature (P<0.001) and to infusion time (P<0.001) (FIG. 5 and Table 2). Indeed, at 50° C., concentration of EGCG is relatively low in comparison with higher temperatures, increasing from 0 µg/mL at 0 min, to 15.5 µg/mL at 5 min, 77.2 µg/mL after 10 min, 245.3 µg/mL at 20 min to finally reach the maximum concentration of 489.3 µg/mL at 40 min ($R2=0.999$). At 90° C., the EGCG concentration increases constantly from 0 µg/mL at 0 min, to 1071.4 µg/mL after a 40 min infusion ($R2=0.983$). It was interesting to note that at temperatures of 50° C. or 60° C. and for an infusion time inferior to 10 min, the solubilisation of EGCG is minimal whereas at higher temperatures, such as 70, 80 or 90° C., higher concentration of EGCG are obtained.

(−)-Gallocatechin Gallate (GCG) Concentration

Figure 6:
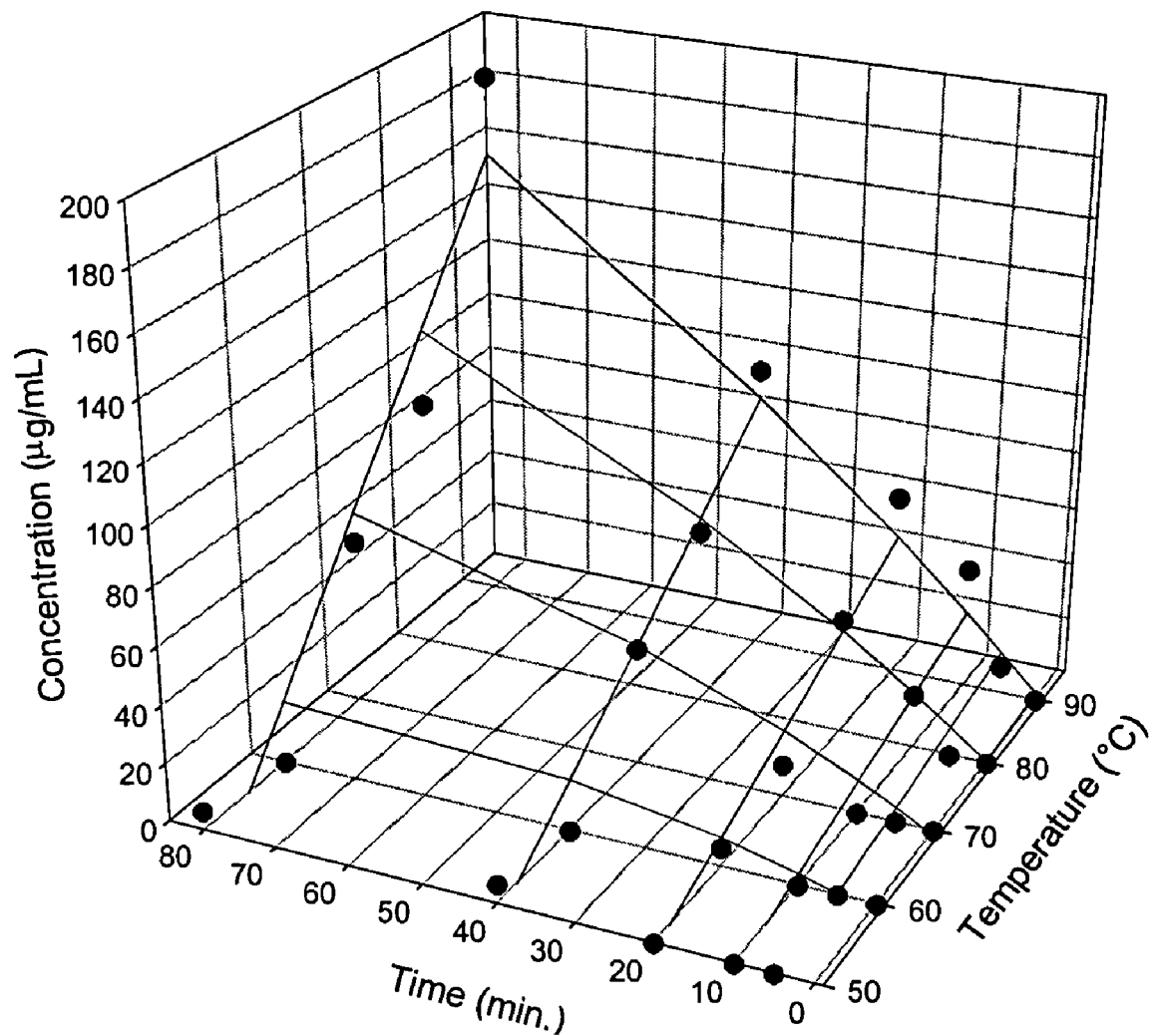
FIG. 6 shows the variation of gallocatechin gallate (GCG) concentration of a green tea infusion as a function of brewing time and brewing temperature.

Solubilisation of GCG increases importantly with infusion temperature (P<0.001) and less importantly with infusion time (P<0.001) (FIG. 6 and Table 2). At 50° C. and 60° C., GCG concentration is below or at the limit of detection of our method. At 70° C., GCG concentration remains pratically nil up to 20 minutes of infusion, to further increase to 40.6 µg/mL at 40 min and to 57.2 µg/mL at 80 min of infusion ($R2=0.998$). At 90° C., GCG concentration varies from 0 µg/mL a 0 min to 63.5 µg/mL at 20 min, to further increase to 186.0 µg/mL after a 80 min infusion ($R2=0.989$).

(−)-Epicatechin Gallate (ECG) Concentration

Figure 7:
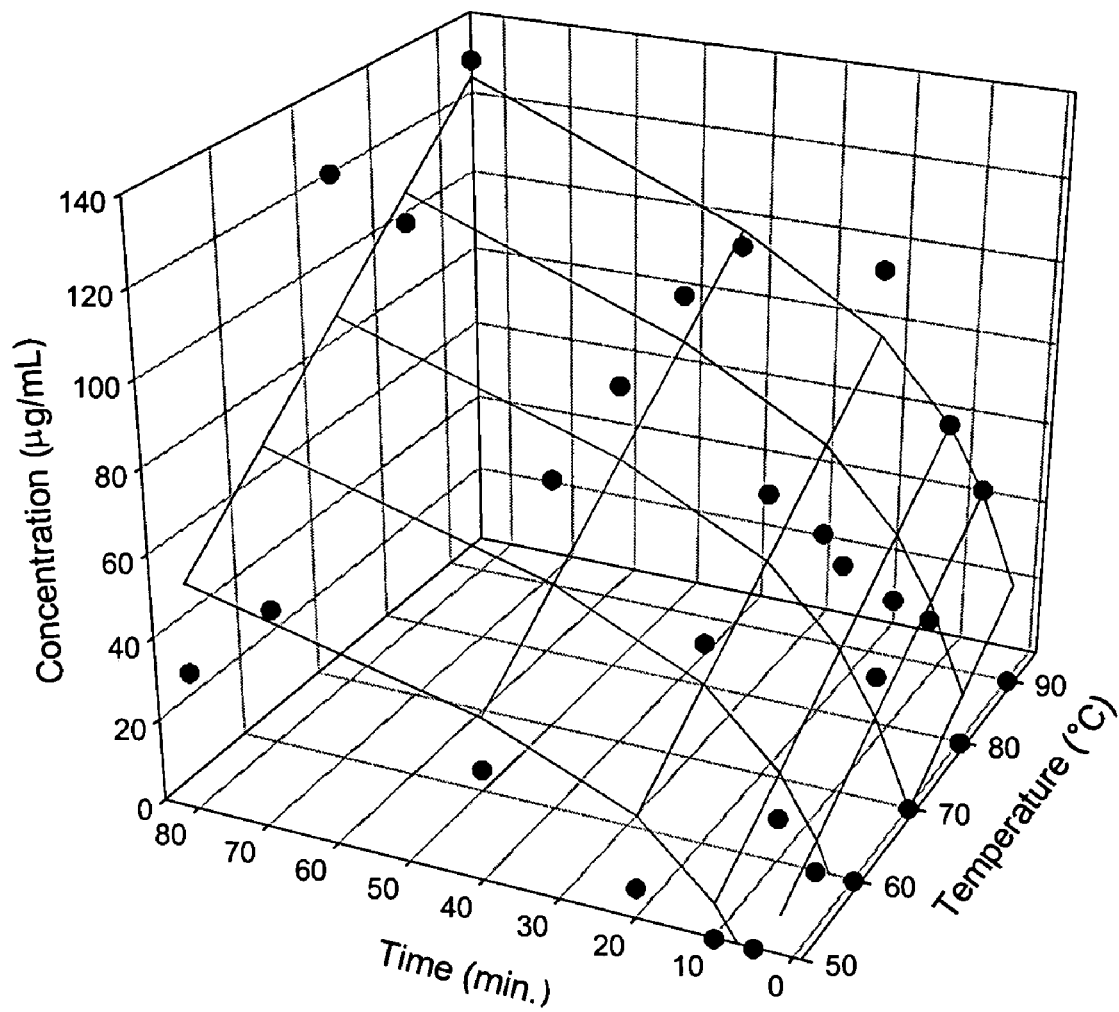
FIG. 7 shows the variation of epicatechin gallate (ECG) concentration of a green tea infusion as a function of brewing time and brewing temperature.

ECG concentration is modulated by temperature (P<0.001) and by infusion time (P<0.001) (FIG. 7 and Table 2). At 50° C. ECG concentration is 0 µg/mL at 0 min and remains undetectable until 20 minutes where it reaches a concentration of 7.6 µg/mL, to further increase to 33.9 µg/mL at 80 min ($R2=0.998$). At 90° C., ECG concentration varies from 0 µg/mL at 0 min to 133.9 µg/mL after a 80 min infusion ($R2=0.945$).

Total Catechins

Our results showed that an infusion performed for 5 minutes leads to the extraction of 499.69 µg/mL of catechins at 50° C., 1059.51 µg/mL at 70° C. and 341.48 µg/mL at 90° C. Therefore, there exists a correlative association between the brewing temperature and the concentration of catechins. Brewing time also modulates the total concentration of catechins. An infusion at 50° C. leads to the extraction of 499.69 µg/mL of catechins after 5 min, 911.47 µg/mL after 10 min, 1382.43 µg/mL after 20 min, 1917.81 µg/mL after 40 min and 1901.40 µg/1 nL after 80 min. Similar results were obtained at higher temperatures (at 70° C.: 5 min infusion, 1959.51 µg/mL of catechins; 10 min, 1665.59 µg/mL; 20 min, 1737.00 µg/mL; 40 min, 2499.68 µg/mL and 80 min, 2794.48 µg/mL).

Statistical Analysis

Variance analysis showed that solubilization of flavanols and caffeine is dependent on infusion time (P<0.001) and, for some compounds, on the brewing temperature (P<0.001) (Table 3). Every 3D curve illustrating the concentration of catechins and caffeine respectively to infusion time and infusion temperature corresponds to the general formula, where t is time and T temperature:

$$f(t, T) = t_0 + \frac{a}{\left[1 + e^{\left(-\frac{(T-T_0)}{b}\right)}\right]} + c*t + d*t*T$$

TABLE 3

| | Constant value (cte) of 3D modelisation formula | | | | | | |
|---|---|---|---|---|---|---|---|
| | EGC cte | C cte | Caff cte | EC cte | EGCG cte | GCG cte | ECG cte |
| x0 | 994.8240 | −4.4060 | 132.4960 | 118.5000 | −131.7120 | −642.9220 | −38.0160 |
| y0 | −12.4198 | 51.1742 | −9.7377 | −13.1509 | 0.4293 | 72.7539 | −35.7328 |
| a | −9102.2240 | 1.4240 | −3087.3040 | −1387.3860 | −1408.7580 | 825.7660 | −1428.5940 |
| b | −6.3225 | −0.3074 | −4.6031 | −5.7561 | −7.7722 | −63.7721 | −10.9074 |
| c | 1.9700 | 0.1120 | 2.8820 | 0.1640 | 12.3120 | 0.2180 | 1.2800 |
| d | 0.0120 | 0.0020 | 0.0120 | 0.0020 | 0.0480 | 0.0540 | 0.0080 |
| $R^2$ | 0.941 | 0.809 | 0.904 | 0.921 | 0.912 | 0.911 | 0.831 |
| Prob* | <0.0001 | <0.0001 | <0.0001 | <0.0001 | <0.0001 | <0.0001 | <0.0001 |

*Meaning level of model following variance analysis

Example 2

Determination of the Catechin Content of a Sequential Brewing Process

Method

Protocol 20 g of green tea were brewed in 1000 mL of double-distilled water to perform catechin solubilization. A 1:50 tea:water ratio was respected as mentioned in the art. The first brewing step was carried out at 50° C. for 10 minutes in a thermostated water-bath. The green tea was removed from the solution and gently squeezed to extract as much water possible. The green tea was then soaked for 10 minutes, for the second brewing step, in 1000 mL of double-distilled water preheated at 80° C. The two-step extraction procedure was repeated three times. After each 10-minutes brewing step the solution was collected. 1.5 mL-samples of both solutions were used for HPLC catechin concentration determination, while the remaining solutions were freeze-dried for 24 hours at room temperature (Model Freezone 4.5, Labconco, Kansas City, Mich., U.S.A.). The lyophilized catechin extracts were stored at 4° C. before chemical composition analyses were performed.

Determination of Catechin Concentration

Catechin concentration was determined by HPLC, following the methodology described hereinabove.

Ash Content of the Extracts

Approximately 1.0 g of lyophilized extract was added to the cooled crucibles, and the mass was recorded. The sample was then ashed at 650° C. for 16 hours, cooled down and weighed at room temperature. Crucibles were washed beforehand in hydrochloric acid (HCl, 10%) for two hours, rinsed with deionized water and dried for one hour in an oven at 550° C. Crucibles were removed from the oven and placed in a dessicator for 30 minutes. For lyophilized isolates, approximately 1.0 g of lyphilized extract was added to the cooled crucibles, and the mass was recorded. The samples were then dried overnight in a vacuum oven at 100° C. The samples were cooled in a dessicator for 30 minutes and weighed when they reached room temperature.

Results

Catechins and Caffein concentration

Figure 8:
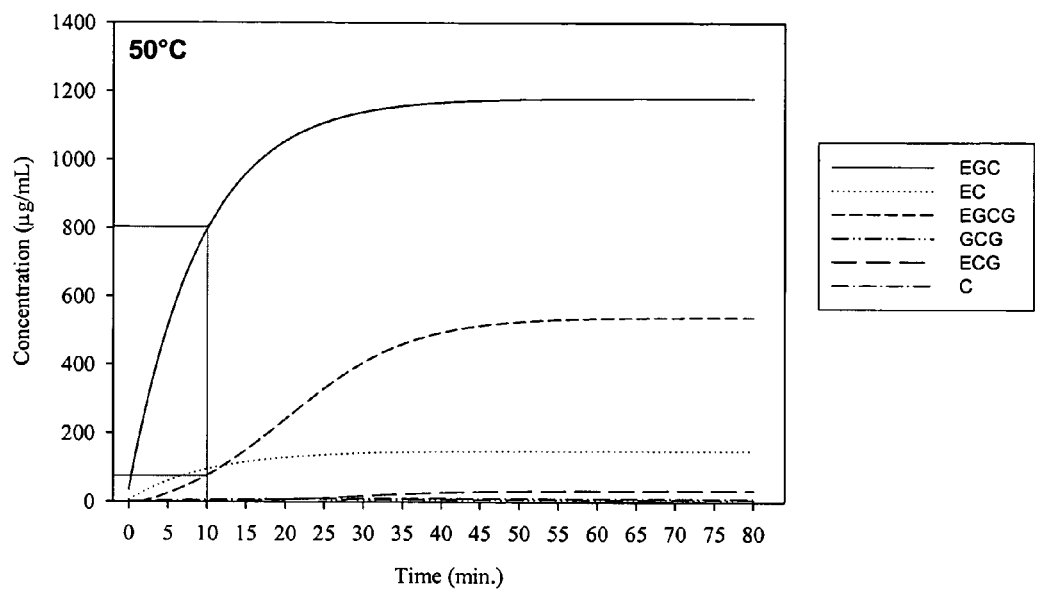
FIGS. 8a) to 8b) show the concentration variation of catechins in a green tea infusion as a function of brewing time at 50° C. and 90° C., respectively.
Figure 8:
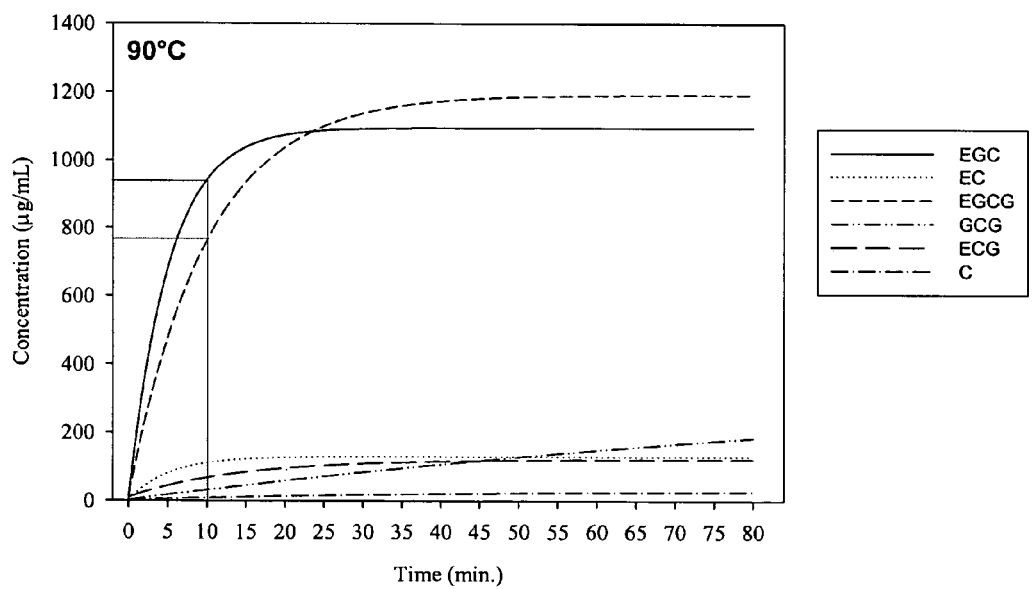

According to the HPLC data obtained it appears that the solutions obtained after each extraction step were very different in catechin composition (FIGS. 8a and 8b and Table 4). EGC represented 78.9% of the total catechin in the first extraction step solution while its concentration decreased to 39.5% in the second extraction step. On the contrary, the second main catechin, EGCG, has its concentration increasing from 153.7 µg/mL (10.8% of the total catechin) in the first solution to 503.0 µg/mL (47.6%) in the second one: its concentration was increased three times while the EGC concentration was decreased approximately by one third. The C and EC contents were quite stable with respective averaged concentration of 0.55% and 7.25% of the total catechins. Furthermore, GCG and ECG which presented inexistent or very low concentrations in the first step extraction solution, had had their concentrations increasing. In the second extraction step, GCG and ECG concentrations represented respectively 2.6 and 4.7% of the total catechin content. The concentration of caffein in both solutions was relatively constant with an averaged concentration of 230.5 µg/mL. These results confirm the fact that it is possible to concentrate the EGCG compound by brewing tea in a two step extraction. Moreover, in comparison with previous results aiming at optimizing the solubilization of catechins, the EGCG extracted in the second extraction represented 78% of the total EGCG solubilized during a long term brewing: the yield of extraction in the second step is very high.

TABLE 4

Concentration (in µg/mL) of catechins and caffein in solution after the first and second step extraction procedure.

|  | First step extraction | Second step extraction |
|---|---|---|
| EGC | 1122.2 ± 98.6 | 417.8 ± 15.4 |
| C | 8.82 ± 0.47 | 4.56 ± 0.55 |
| EC | 133.7 ± 7.1 | 53.5 ± 3.0 |
| EGCG | 153.7 ± 40.1 | 503.0 ± 47.2 |
| GCG | 0 ± 0 | 28.0 ± 2.0 |
| ECG | 3.99 ± 0.01 | 50.1 ± 7.6 |
| Caffein | 252.0 ± 12.3 | 209.7 ± 9.9 |

Extract Composition:

As previously observed from HPLC data, the extract compositions were very different (Table 5). In the first extraction, the total catechins represented 37.5% of the total extract and this concentration increased to 52.8% of the total composition in the second extract. Caffeine represented 6.6% of the total composition in the first extract and 10.5% in the second. The ash content was decreased during the two-step extraction process from 9.76 to 5.88%. The product was then purified in catechins and the percentage of the main catechins was changed. EGC represented 29.5% of the total extract in the first extract while in the second extract, its concentration decreased to 21%. For EGCG, its concentration increased from 4.0% to 25% between the first and the second extraction step. According to these results, its appeared that gallated phenolic compounds were mainly extracted in the second phase of the procedure while the non-gallated phenolic compounds were extracted during both phases of the process. The fact that the ash content decreased during the second step, was due to the fact that the mineral which were present at the surface and in the green tea leaves rapidly solubilized in the first minute of brewing. Consequently, they were recovered during the first phase and were more present in the first extract. The ash content was two times more concentrated in the first extract than in the second one. This is another advantage of the process which led to an extract with a higher purity.

TABLE 5

Total solids and ash content, and concentration of catechins and caffein in solution after the first and second step of the extraction procedure.

|  | First step extract | Second step extract |
|---|---|---|
| Total solid content (%) | 96.42 ± 0.22 | 98.04 ± 0.31 |
| Ashes (% dry basis) | 9.76 ± 0.19 | 5.88 ± 0.30 |
| EGC (mg/g extract on dry basis) | 295.3 | 208.9 |
| C (mg/g extract on dry basis) | 2.4 | 2.3 |
| EC (mg/g extract on dry basis) | 35.2 | 26.7 |
| EGCG (mg/g extract on dry basis) | 40.5 | 251.5 |
| GCG (mg/g extract on dry basis) | 0.0 | 14.0 |
| ECG (mg/g extract on dry basis) | 1.1 | 25.0 |
| Caffein (mg/g extract on dry basis) | 66.3 | 105.0 |

It appeared from these results that it was possible to produce, in a simple way, an EGCG-enriched fraction from green tea containing 25% of EGCG. In fact, a two step brewing procedure based on the temperature dependent solubilization of both major catechin EGC and EGCG allowed the production of such an extract by decreasing its ash and EGC contents during the second step extraction. The EGCG concentration in this extract represented 78% of the total solubilizable EGCG.

This simple process could be greatly improved by demineralizing this EGCG-enriched fraction either by dialysis or electrodialysis. Moreover, this enriched fraction should be tested for its nutraceutical properties in order to improve its potential health applications. In addition, the GCG and ECG which were not present or only in trace in the first extract, appeared in a higher concentration in the second extract.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method for obtaining an aqueous catechin fraction enriched in epigallocatechin gallate from a green tea leaf, said aqueous catechin fraction having a higher concentration of epigallocatechin gallate than a concentration of epigallocatechin, said method comprising the steps of:
   a) submitting said green tea leaf to a first brew at a first brew temperature of between 20° C. and 60° C. for a period of between 5 and 80 minutes, thereby extracting epigallocatechin from said green tea leaf into said first brew;
   b) discarding the first brew from step a) and collecting the green tea leaf as treated in step a);
   c) submitting the green tea leaf collected in step b) to a second brew at a second brew temperature of between 70° C. and 90° C. for a period of between 5 and 80 minutes, thereby extracting epigallocatechin gallate from said green tea leaf into said second brew; and
   d) collecting the second brew from step c), said second brew being the aqueous catechin fraction enriched in epigallocatechin gallate.

2. The method of claim 1, wherein the period of step a) is of 10 minutes, and wherein the period of step c) is of 10 minutes.

3. The method of claim 1, wherein the total catechin of the aqueous catechin fraction comprises at least 25% of epigallocatechin gallate.

4. A method for obtaining an aqueous catechin fraction enriched in epigallocatechin gallate from a green tea leaf; said aqueous catechin fraction having a higher concentration of epigallocatechin gallate than a concentration of epigallocatechin, said method consisting essentially of the steps of:
   a) submitting said green tea leaf to a first brew at a first brew temperature of between 20° C. and 60° C. for a period of between 5 and 80 minutes, thereby extracting epigallocatechin from said green tea leaf into said first brew;
   b) discarding the first brew from step a) and collecting the green tea leaf as treated in step a);
   c) submitting the green tea leaf collected in step b) to a second brew at a second brew temperature of between 70° C. and 90° C. for a period of between 5 and 80 minutes, thereby extracting epigallocatechin gallate from said green tea leaf into said second brew; and
   d) collecting the second brew from step c), said second brew being the aqueous catechin fraction enriched in epigallocatechin gallate.

5. The method of claim 4, wherein the period of step a) is of 10 minutes, and wherein the period of step c) is of 10 minutes.

6. The method of claim 4, wherein the total catechin of the aqueous catechin fraction comprises at least 25% of epigallocatechin gallate.

7. A method for obtaining an aqueous catechin fraction enriched in epigallocatechin gallate from a green tea leaf; said aqueous catechin fraction having a higher concentration of epigallocatechin gallate than a concentration of epigallocatechin, said method consisting of the steps of:
   a) submitting said green tea leaf to a first brew at a first brew temperature of between 20° C. and 60° C. for a period of between 5 and 80 minutes, thereby extracting epigallocatechin from said green tea leaf into said first brew;
   b) discarding the first brew from step a) and collecting the green tea leaf as treated in step a);
   c) submitting the green tea leaf collected in step b) to a second brew at a second brew temperature of between 70° C. and 90° C. for a period of between 5 and 80 minutes, thereby extracting epigallocatechin gallate from said green tea leaf into said second brew; and
   d) collecting the second brew from step c), said second brew being the aqueous catechin fraction enriched in epigallocatechin gallate.

8. The method of claim 7, wherein the period of step a) is of 10 minutes, and wherein the period of step c) is of 10 minutes.

9. The method of claim 7, wherein the total catechin of the aqueous catechin fraction comprises at least 25% of epigallocatechin gallate.

* * * * *